US006393726B1

(12) United States Patent
Momose et al.

(10) Patent No.: US 6,393,726 B1
(45) Date of Patent: May 28, 2002

(54) METHOD FOR ABSORBING MOISTURE OF COMPOSITE MATERIAL

(75) Inventors: Yutaka Momose; Shunichi Bandoh, both of Kakamigahara; Hirohito Hira, Nagoya, all of (JP)

(73) Assignee: Kawasaki Jukogyo Kabushiki Kaisha, Kobe (JP)

( * ) Notice: Subject to any disclaimer, the term of this patent is extended or adjusted under 35 U.S.C. 154(b) by 0 days.

(21) Appl. No.: 09/626,910

(22) Filed: Jul. 27, 2000

(30) Foreign Application Priority Data

Jul. 28, 1999 (JP) .......................... 11-214274

(51) Int. Cl.[7] .............................. F26B 3/00
(52) U.S. Cl. .................................. 34/329; 428/297.4
(58) Field of Search ..................... 34/329, 303, 342, 34/398; 156/64, 89.22; 428/297.4, 323, 392; 525/72; 524/493

(56) References Cited

U.S. PATENT DOCUMENTS

| 3,664,188 A | | 5/1972 | Kockott |
| 4,537,917 A | * | 8/1985 | Hergenrother ............... 523/209 |
| 4,562,115 A | * | 12/1985 | Hergenrother ............... 428/392 |
| 5,242,976 A | * | 9/1993 | Strassel et al. ................ 525/72 |
| 5,264,279 A | * | 11/1993 | Imamura et al. ............. 428/323 |
| 5,384,196 A | * | 1/1995 | Inoue et al. ................. 428/411.1 |
| 5,680,713 A | * | 10/1997 | Forbert et al. ................ 34/342 |
| 5,718,059 A | * | 2/1998 | Banerjee et al. .............. 34/398 |
| 5,893,955 A | * | 4/1999 | Rousseau et al ......... 156/89.22 |
| 5,954,898 A | * | 9/1999 | McKague et al. ............ 156/64 |
| 5,985,431 A | * | 11/1999 | Oosedo et al. ............ 428/297.4 |
| 6,071,997 A | * | 6/2000 | Tanaka et al. ................ 524/493 |
| 6,092,302 A | * | 7/2000 | Berrigan ....................... 34/303 |

FOREIGN PATENT DOCUMENTS

| EP | 0026981 | 4/1981 | |
| JP | 62-101421 | 11/1987 | |
| JP | 63-169538 | 7/1988 | |
| JP | 02 010133 | 1/1990 | |
| JP | 02001041947 | * 2/2001 | .......... G01N/33/00 |

* cited by examiner

Primary Examiner—Teresa Walberg
Assistant Examiner—Leonid M Fastovsky
(74) Attorney, Agent, or Firm—Oliff & Berridge PLC

(57) ABSTRACT

A method for absorbing the moisture of a composite material, which can absorb the moisture of the composite material in a short period of time and which can provide a moisture absorption distribution which is equal to that of a composite material placed under actual environment. At time table, having a plurality of different environment conditions for pressure, temperature and humidity, and periods of time corresponding to the environment conditions, is previously prepared. Then, a composite material is put in a pressure vessel, and the environmental conditions in the pressure vessel are changed on the basis of the time table. Thus, the moisture absorption state of the composite material can be equal to that after the elapse of predetermined years under actual environment. In addition, it is possible to absorb the moisture of the composite material in a short period of time by absorbing the moisture of the composite material under an environment condition of high pressure.

14 Claims, 3 Drawing Sheets

METHOD FOR ABSORBING MOISTURE OF COMPOSITE MATERIAL

BACKGROUND OF THE INVENTION

1. Field of the Invention

The present invention relates generally to a method for absorbing the moisture of a composite material so that the composite material is in a moisture absorption state, which is equal to that of a composite material after the elapse of predetermined years under actual environment, when a test for evaluating the strength of the composite material is conducted.

2. Description of Related Background Art

With respect to the composite material structure of airplanes, it is required to insure a predetermined strength after the elapse of a predetermined useful life, so that it is required to reproduce a composite material, which is equal to a composite material after the elapse of predetermined years, e.g., 25 years, under actual environment, to conduct a test for evaluating the strength of the reproduced composite material. The moisture absorption state of a composite material after the elapse of predetermined years under actual environment is greatly different from that of a new composite material. This moisture absorption state of the composite material has a great influence on the strength of the composite material. Therefore, in order to conduct a test for evaluating the strength of a composite material, it is required to conduct the test in a moisture absorption state which is equal to that of a composite material which is placed under actual environment.

In order to obtain a composite material of such a high moisture absorption state, a composite material is conventionally placed under a high humidity environment, which includes a temperature of 71° C. and a relative humidity of 95%RH or higher under atmospheric pressure, for several weeks so that the total quantity of moisture absorption is equal to that of a composite material under actual environment.

The composite material structure has a thick-wall portion having a thickness of 10 mm or more. usually, this thick-wall portion serves as a strength evaluated portion. In recent years, the thickness of the thick-wall portion of the composite material structure for use in airplanes increases, so that the moisture absorption period required to obtain a moisture absorption state, which is equal to that under actual environment, extends over a long period of time, e.g., there are some cases where a moisture absorption period of tens weeks to one year is required. Thus, there is a problem in that the development period extends over a long period of time. Therefore, it is desired to provide a method for absorbing the moisture of a composite material, which can absorb the moisture of the composite material in a short period of time.

In addition, there is a problem in that the moisture absorption distribution of a composite material placed under actual environment is different from that of a composite material which was moisture-absorbed in a short period of time.

FIG. 4 is a graph showing the moisture absorption distribution of a composite material in directions perpendicular thereto, wherein line 1 shows the moisture absorption distribution of a composite material after the elapse of 25 years under actual environment, and line 2 shows the moisture absorption distribution of a composite material which was moisture-absorbed for 36 weeks under a high humidity environment including a relative humidity of 95%RH. Furthermore, the axis of ordinates denotes the percentage of a coefficient of moisture absorption to the maximum coefficient of moisture absorption, which shows the moisture content of a composite material per unit weight. The axis of abscissas denotes the distance from the surface of the composite material, which denotes the distance from the surface to the center of the composite material, i.e., to 10 mm, since the thickness of the composite material is 20 mm.

As can be seen from this graph, the difference between the coefficients of moisture absorption of the surface and central portion of the composite material under actual environment is not so great, whereas the difference between the coefficients of moisture absorption of the surface and central portion of the composite material, which was moisture-absorbed in a short period of time under a high humidity environment, is greater. That is, the composite material, which was moisture-absorbed in a short period of time, can not accurately reproduce the moisture absorption state of the composite material under actual environment. Therefore, there is a problem in that the strength of the composite material, which is moisture-absorbed by the conventional moisture-absorbing method, can not be accurately evaluated as the thickness thereof increases. In particularly such a problem is remarkably caused in the case of a composite material having a thickness of 10 mm or more.

SUMMARY OF THE INVENTION

It is therefore an object of the present invention to eliminate the aforementioned problems and to provide a method for absorbing the moisture of a composite material, which can absorb the moisture of the composite material in a short period of time and which can provide a moisture absorption distribution which is equal to that of a composite material which is placed under actual environment.

In order to accomplish the aforementioned and other objects, according to one aspect of the present invention, there is provided a method for absorbing the moisture of a composite material under a high humidity environment so that the moisture absorption state of the composite material is equal to the moisture absorption state of a composite material after the elapse of predetermined years under actual environment, wherein the moisture of the composite material is absorbed in a pressure container at a predetermined high temperature, a predetermined high humidity and a predetermined high pressure.

The predetermined high temperature may be a temperature below the glass transition point of the composite material.

The predetermined high temperature is preferably a temperature which is higher than 50° C. and lower than 140° C. when the composite material is made of an epoxy resin.

The predetermined high humidity may be a relative humidity of 70%RH or higher to 100%RH or lower.

The predetermined high pressure may be a pressure in the range of from 1400 hPa to 5000 hPa.

The predetermined high pressure is preferably a pressure in the range of from 1400 hPa to 3000 hPa.

According to another aspect of the present invention, there is provided a method for absorbing the moisture of a composite material under a high humidity environment so that the moisture absorption state of the composite material is equal to the moisture absorption state of a composite material after the elapse of predetermined years under actual environment, wherein the moisture of the composite material is absorbed in a pressure container at a predetermined high temperature of the glass transition point of the composite material or lower, a predetermined high humidity of a relative humidity in the range of from 70%RH to 100%RH, and a predetermined high pressure of higher than atmospheric pressure.

According to a further aspect of the present invention, there is provided a method for absorbing the moisture of a composite material under a high humidity environment so that the moisture absorption state of the composite material is equal to the moisture absorption state of a composite material after the elapse of predetermined years under actual environment, wherein the composite material in a pressure vessel, and the temperature, humidity and pressure in the pressure vessel are changed in accordance with a predetermined time table so that the moisture absorption distribution of the composite material in directions perpendicular thereto is equal to that of a composite material after the elapse of predetermined years under actual environment.

The time table may be prepared by a numerical operation using an equation indicative of Fick law, Arrhenius equation, an equation indicative of the relationship between a relative humidity and a saturated coefficient of moisture absorption, and an equation indicative of the relationship between a coefficient of moisture absorption and a moisture concentration.

According to the present invention, it is possible to provide a desired moisture absorption distribution by changing conditions for temperature, humidity and pressure in a pressure vessel. Thus, it is possible to obtain a composite material having a required moisture absorption distribution which is equal to that of a composite material after the elapse of predetermined years under actual environment, and it is possible to accurately evaluate the strength of a composite material even if the composite material has a great thickness.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, a preferred embodiment of a method for absorbing the moisture of a composite material according to the present invention will be described below.

The composite materials for use in this preferred embodiment include resin composite materials for use in airplanes, e.g., rotor hubs of helicopters. The resin composite materials supposed in this preferred embodiment include fiber reinforced composite materials. The resins include epoxy resins, and the reinforcing fibers include glass fibers. In other preferred embodiments, the resins of the composite materials may include polyimide resins, bismaleimide resins and phenol resins, and the reinforcing resins may include carbon fibers, ceramic fibers and alamide fibers.

With respect to the composite materials for use in airplanes, it is required to conduct a strength evaluating test, such as a bending test and a tension test, using a composite material which is in a moisture absorption state equal to that after the elapse of predetermined years under actual environment, so that it is required to absorb the moisture of the composite material in a short period of time.

Figure 1:
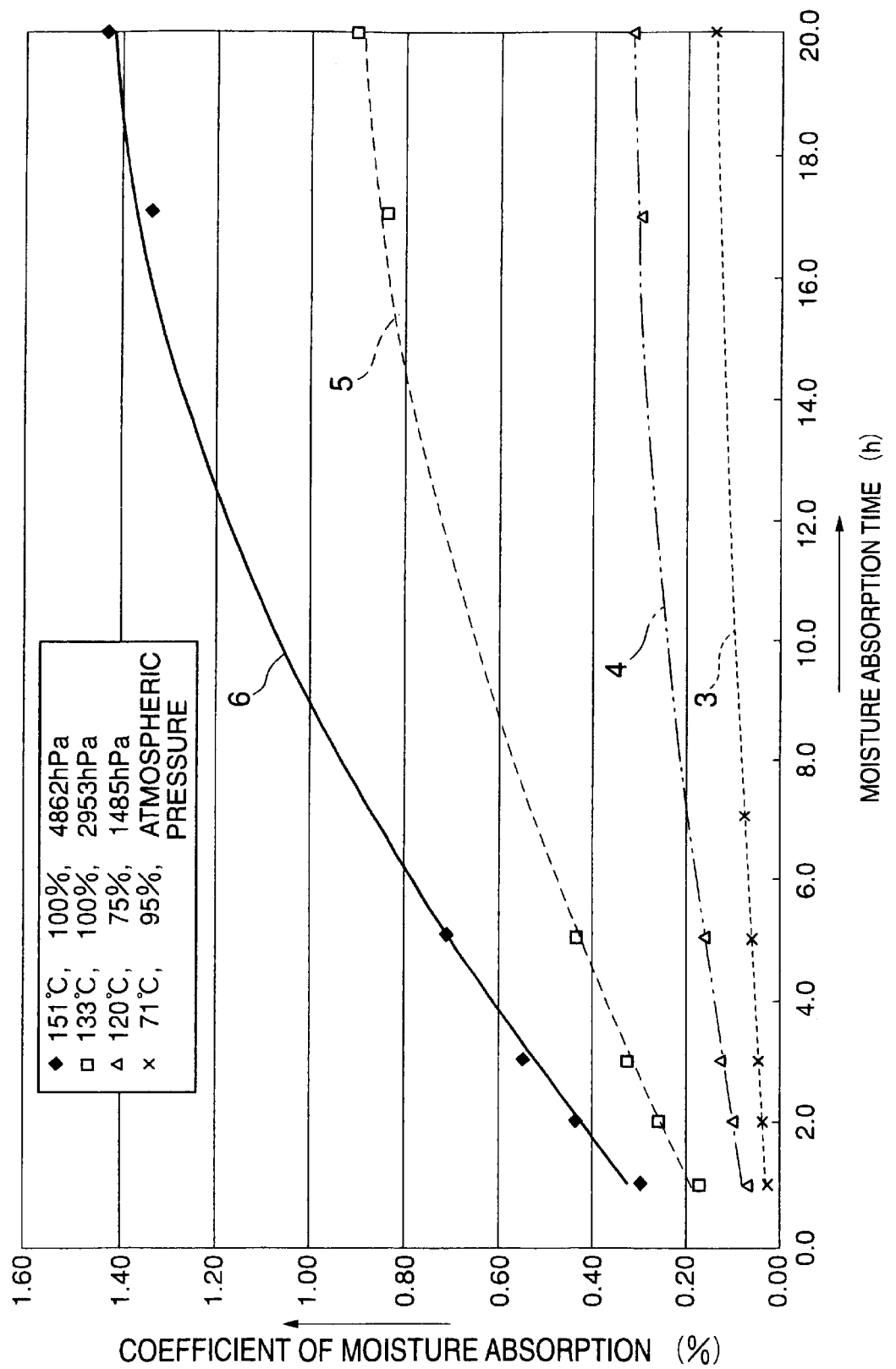
FIG. 1 is a graph showing the relationship between the moisture absorption time and the coefficient of moisture absorption under various environments.

FIG. 1 is a graph showing the relationship between the moisture absorption time and coefficient of moisture absorption of a composite material under various environments. In FIG. 1, the axis of abscissa denotes the moisture absorption time (h), and the axis of ordinates denotes the coefficient of moisture absorption (%). In this test, each of a plurality of plate test pieces is put in a pressure vessel, which is maintained on a predetermined pressure condition, and the weight of each of the test pieces is measured after the elapse of a predetermined time to obtain a coefficient of moisture absorption. In FIG. 1, line 3 is a graph on the same environmental conditions as those in the conventional moisture-absorbing method, i.e., on environmental conditions including a pressure of atmospheric pressure, a temperature of 71° C. and a relative humidity of 95%RH, and line 4 is a graph on environmental conditions including an absolute pressure of 1485 hPa, a temperature of 120° C. and a relative humidity of 75%RH. In addition, line 5 is a graph on environmental conditions including an absolute pressure of 2953 hPa, a temperature of 133° C. and a relative humidity of 100%RH, and line 6 is a graph on environmental conditions including an absolute pressure of 4852 hPa, a temperature of 151° C. and a relative humidity of 100%RH.

It can be seen from the comparison of lines 3 through 6 that the coefficient of moisture absorption considerably increases as temperature and pressure increase. That is, it is possible to absorb the moisture of the composite material in a shorter period of time as temperature and pressure increase.

It can be also seen from the comparison of lines 3 and 4 that the moisture of the composite material is more easily absorbed at a higher temperature even if the relative humidity is low.

As can be seen from the above described experimental results, it is possible to absorb a predetermined amount of moisture of the composite material in a short period of time by absorbing the moisture of the composite material in the pressure vessel which is maintained at a high temperature and a high pressure. Furthermore, in this preferred embodiment, the high pressure is in the range of from 1400 hPa to 5000 hPa, preferably in the range of from 1400 hPa to 3000 hPa. If an epoxy resin is used as the resin of the composite material, the high temperature is selected so as not to exceed about 140° C. which is the glass transition point of the epoxy resin. For example, the high temperature is selected so as to be in the range of from 50° C. to 130° C. Therefore, the temperature condition is suitably changed in accordance with the kind of the composite material.

The pressure distribution of the composite material will be described below.

As described above, a composite material having a quantity of moisture absorption, which is equal to that of a composite material after the elapse of predetermined years, e.g., 25 years, under actual environment, can be obtained in a short period of time by absorbing the moisture of the composite material under a high humidity environment using a pressure vessel.

However, as described in the description of the prior art, if the thickness of the composite material increases, the moisture absorption distribution of the composite material in the directions perpendicular thereto is different from that of a composite material under actual environment even if the quantity of moisture absorption is the same. In particular, the composite material supposed in this preferred embodiment is used for rotor hubs of helicopters, and has a thickness of about 20 to 40 mm, so that the moisture absorption distribution is greatly different only by equalizing the quantity of moisture absorption.

Therefore, according to the present invention, the environment conditions in the pressure vessel are changed in a predetermined time table so as to also equalize the moisture absorption distribution. This time table uses the following basic equations (1) through (5) so as to obtain a predetermined moisture absorption distribution, and is determined by simulating the distribution by means of a computer.

Basic Equations
Fick law $$J = -D\frac{\partial C}{\partial x} \quad (1)$$

$$D\frac{\partial 2C}{\partial x2} = \frac{\partial C}{\partial \tau} \quad (2)$$

Arrhenius equation $$D = D_0 \exp\left(-\frac{A}{T}\right) \quad (3)$$

Relationship Between Relative Humidity And Saturated Coefficient Of Moisture Absorption $$Me = Mm\left(\frac{\phi}{100}\right)b. \quad (4)$$

Relationship Between Coefficient Of Moisture Absorption And Moisture Concentration $$M = \frac{C}{\rho_c} \times 100 \quad (5)$$

A: Constant
b: Constant
C: Moisture Concentration
D: Moisture Diffusion Coefficient
D: Constant
J: Flow Velocity Of Moisture
M: Coefficient Of Moisture Absorption
A: Saturated Coefficient Of Moisture Absorption
M: Maximum Coefficient Of Moisture Absorption
T: Absolute Temperature
x: Coordinates In Perpendicular Directions
$\phi$: Relative Humidity
$\rho_c$: Density Of Composite Material
$\tau$: Time In FIG. 2, line 7 is a graph showing a moisture absorption distribution simulated by a computer in accordance with an example of a time table which is determined on the basis of the above described basic equations (1) through (5), and line 8 is a graph showing a moisture absorption distribution simulated by a computer with respect to a composite material after the elapse of 25 years under actual environment. In the time table for use therein, a first environment condition including a relative humidity of 80%RH and a pressure of atmospheric pressure is held for 36 weeks, and a second environment condition including a relative humidity of 70%RH and a pressure of atmospheric pressure is held for 8 weeks. Furthermore, in this simulation, assuming that the thickness of the composite material is 20 mm, the axis of abscissa of the graph denotes the distance from the surface of the composite material to the center, i.e., 10 mm, and the axis of ordinates thereof denotes the coefficient of moisture absorption of the composite material assuming that it is 100% in the saturated state.

Figure 2:
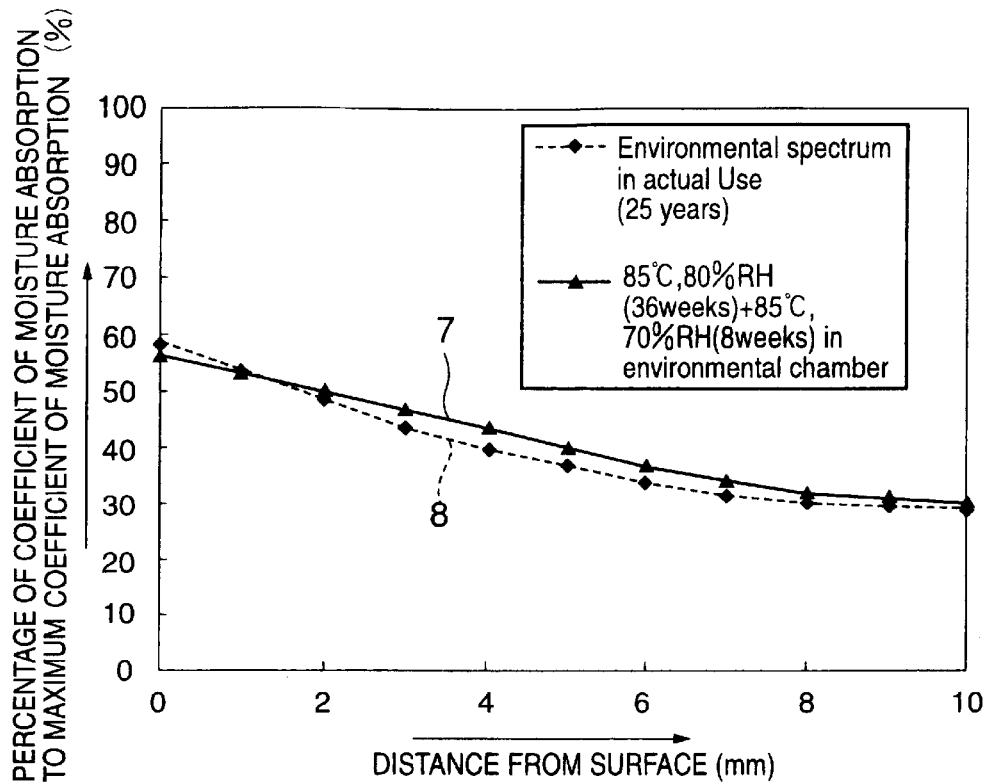
FIG. 2 is a graph showing the moisture absorption distribution of a composite material after the elapse of a predetermined period of time under actual environment, and the moisture absorption distribution of a composite material which is moisture-absorbed on various environmental conditions in accordance with a predetermined time table.
Figure 4:
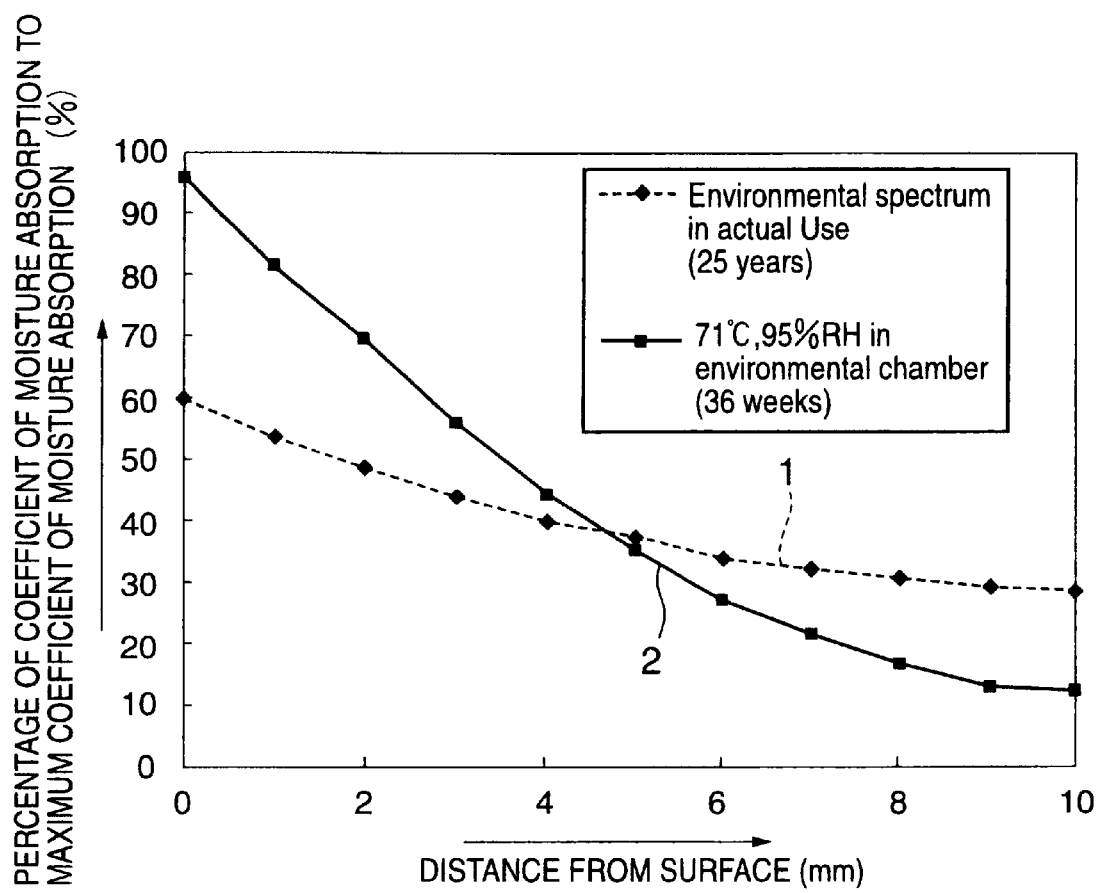
FIG. 4 is a graph showing the moisture absorption distribution of a composite material after the elapse of a predetermined period of time under actual environment, and the moisture absorption distribution of a composite material which is moisture-absorbed by a conventional moisture-absorbing method.

As can be seen from FIG. 2, lines 7 and 8 are substantially the same, and the moisture absorption distribution of the composite material under actual environment is substantially equal to the moisture absorption distribution of the composite material which is moisture-absorbed when the environmental condition in the pressure vessel is changed in accordance with the predetermined time table. This is more clear as compared with the graph of FIG. 4 showing the prior art.

Therefore, if a time table, which comprises a plurality of different environmental conditions for pressure, temperature and humidity, and predetermined periods of time corresponding to the respective environmental conditions, is previously determined by a simulation, and if the environmental conditions in a pressure vessel, in which a composite material is put, are changed on the basis of the time table, it is possible to obtain a composite material having a moisture absorption state which is substantially equal to that of a composite material under actual environment.

Although the first and second environmental conditions are constant at atmospheric pressure in the graph of FIG. 2, the moisture of the composite material can be absorbed under a high humidity environment in a short period of time as shown in FIG. 1. Therefore, if the environmental condition is determined in view of this, it is possible to obtain a composite material having a desired moisture absorption state in a short period of time.

For example, first, the environmental conditions in the pressure vessel are set so as to include a high pressure, and the moisture of a composite material is absorbed by a quantity of moisture absorption which is equal to or higher than the quantity of moisture absorption of a composite material under a desired actual environment. Then, the environmental conditions are changed so as to have a desired moisture absorption distribution. That is, the moisture of the composite material is sufficiently absorbed in a short period of time at the initial stage, and the moisture absorption distribution is adjusted at the next stage. When the initial stage is completed, the moisture absorption distribution is different so that the coefficient of moisture absorption on the surface side is about 100% and the moisture of the central portion is hardly absorbed. At the next stage, the environmental conditions are changed so as to decrease the coefficient of moisture absorption on the surface side and so as to increase the coefficient of moisture absorption of the inner part. Therefore, at this adjusting stage, the pressure is not always a high pressure, but the pressure is sometimes a pressure below atmospheric pressure.

While the time table gradually changing the various environmental conditions has been prepared in the above described moisture-absorbing method, the time table for use in the present invention should not be limited to such a time table gradually and discontinuously changing the environmental conditions, but it may be a time table continuously changing environmental conditions, such as pressure and temperature.

Figure 3:
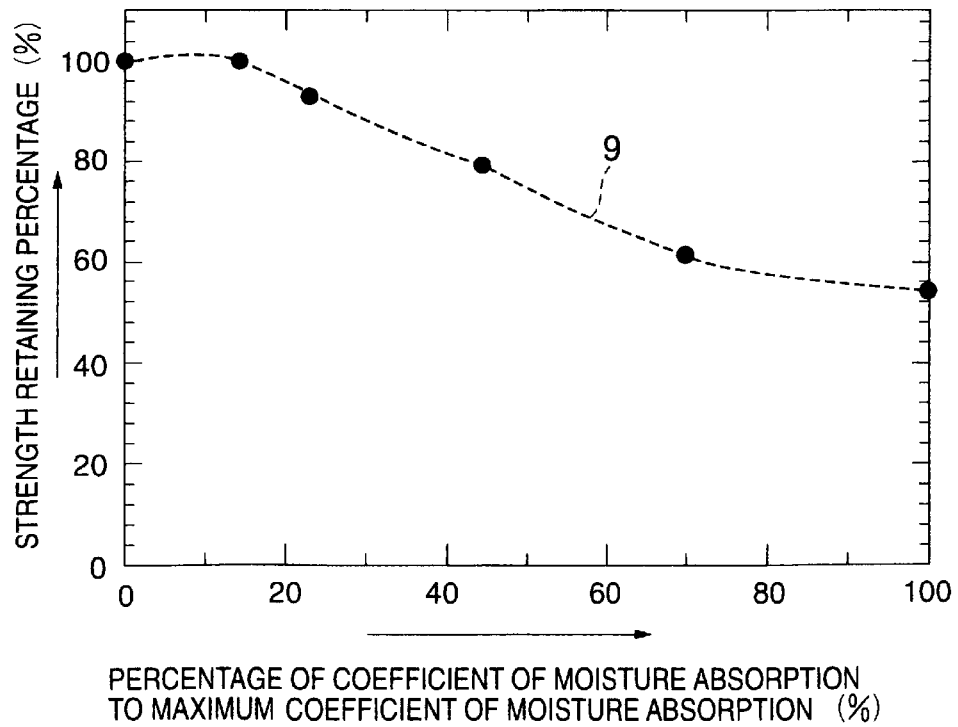
FIG. 3 is a graph showing the relationship between the percentage of a saturate coefficient of moisture absorption to the maximum coefficient of moisture absorption and the strength retaining percentage.

FIG. 3 is a graph showing the relationship between the proportion of the saturated coefficient of moisture absorption to the maximum coefficient of moisture absorption and the strength retaining percentage. As can be seen from line 9 of this graph, there is an intimate relationship between the coefficient of moisture absorption and strength of the composite material, and the strength retaining percentage decreases as the percentage of the saturated coefficient of moisture absorption to the maximum coefficient of moisture absorption increases. Therefore, it can also be seen from the graph of FIG. 3 that it is required to sufficiently take account of the moisture absorption state in the evaluation of the strength of the composite material.

As described above, according to the present invention, by absorbing the moisture of a composite material under a high humidity environment in a pressure vessel, it is possible to absorb the moisture of the composite material to a predetermined quantity of moisture absorption in a shorter period of time than that in the conventional case.

In addition, according to the present invention, it is possible to reduce the moisture absorption period by setting a high temperature, a high humidity and a high pressure on the condition of less than the grass transition point of the complete material.

Moreover, according to the present invention, by changing the environmental condition in the pressure vessel in accordance with the predetermined time table, it is possible to obtain a composite material having a moisture absorption distribution which is equal to a moisture absorption distribution under actual environment.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A method for absorbing moisture into a composite material under a high humidity environment so that a first moisture absorption state of said composite material is equal to a second moisture absorption state of said composite material after the elapse of predetermined years under actual environment, the method comprising:

estimating a predetermined high temperature, a predetermined high humidity and a predetermined high pressure which give the composite material said first moisture absorption state in a predetermined time;

placing the composite material in a pressure container; and subjecting the composite material to the predetermined high temperature, the predetermined high humidity and the predetermined high pressure for the predetermined time in the pressure container, wherein the moisture of said composite material is absorbed in a pressure container at a predetermined high temperature, a predetermined high humidity and a predetermined high pressure.

2. A method for absorbing moisture into a composite material as set forth in claim 1, wherein said predetermined high temperature is a temperature below a glass transition point of said composite material.

3. A method for absorbing moisture into a composite material as set forth in claim 1, wherein said predetermined high temperature is a temperature which is higher than 50° C. and lower than 140° C. when said composite material is made of an epoxy resin.

4. A method for absorbing moisture into a composite material as set forth in claim 1, wherein said predetermined high humidity is a relative humidity of 70%RH or higher to 100%RH or lower.

5. A method for absorbing moisture into a composite material as set forth in claim 1, wherein said predetermined high pressure is a pressure in the range of from 1400 hPa to 5000 hPa.

6. A method for absorbing moisture into a composite material as set forth in claim 5, wherein said predetermined high pressure is a pressure in the range of from 1400 hPa to 3000 hPa.

7. A method for absorbing moisture into a composite material under a high humidity environment so that a first moisture absorption state of said composite material is equal to a second moisture absorption state of said composite material after the elapse of predetermined years under actual environment, the method comprising:

estimating a predetermined high temperature, a predetermined high humidity and a predetermined high pressure which give the composite material said first moisture absorption state in a predetermined time:

placing the composite material in a pressure container; and subjecting the composite material to the predetermined high temperature, the predetermined high humidity and the predetermined high pressure for the predetermined time in the pressure container, wherein the moisture of said composite material is absorbed in the pressure container at the predetermined high temperature of a glass transition point of said composite material or lower, the predetermined high humidity of a relative humidity in the range of from 70%RH to 100%RH, and the predetermined high pressure of higher than atmospheric pressure.

8. A method for absorbing moisture into a composite material under a high humidity environment so that a first moisture absorption state of said composite material is equal to a second moisture absorption state of said composite material after the elapse of predetermined years under actual environment, the method comprising:

estimating a predetermined high temperature, a predetermined high humidity and a predetermined high pressure which give the composite material said first moisture absorption state in a predetermined time;

placing the composite material in a pressure container; and subjecting the composite material to the predetermined high temperature, the predetermined high humidity and the predetermined high pressure for the predetermined time in the pressure container, wherein the predetermined temperature, the predetermined humidity and the predetermined pressure in said pressure vessel are changed in accordance with a predetermined time table so that the moisture absorption distribution into said composite material in directions perpendicular thereto is equal to that into the composite material after the elapse of predetermined years under actual environment.

9. A method for absorbing moisture into a composite material as set forth in claim 8, wherein said time table is prepared by a numerical operation using an equation indicative of Fick law, Arrhenius equation, an equation indicative of the relationship between a relative humidity and a saturated coefficient of moisture absorption, and an equation indicative of the relationship between a coefficient of moisture absorption and a moisture concentration.

10. A method for absorbing moisture into a composite material as set forth in claim 1, wherein said composite material is a resin composite material including a resin for use in an airplane.

11. A method for absorbing moisture into a composite material as set forth in claim 10, wherein said resin is selected from the group consisting of epoxy resins, polyimide resins, bismaleimide resins and phenol resins.

12. A method for absorbing moisture into a composite material as set forth in claim 10, wherein said resin composite material is a fiber reinforced composite material containing a reinforcing fiber.

13. A method for absorbing moisture into a composite material as set forth in claim 12, wherein said reinforcing fiber is selected from the group consisting of glass fibers, carbon fibers, ceramic fibers and alamide fibers.

14. A method for absorbing moisture into a composite material as set forth in claim 1, wherein said composite material has a thickness of 10 mm or more.

* * * * *